United States Patent
Odunsi et al.

(10) Patent No.: US 10,000,546 B2
(45) Date of Patent: Jun. 19, 2018

(54) COMPOSITIONS AND METHOD FOR USE OF RECOMBINANT T CELL RECEPTORS FOR DIRECT RECOGNITION OF TUMOR ANTIGEN

(71) Applicant: Health Research, Inc., Buffalo, NY (US)

(72) Inventors: Kunle Odunsi, Williamsville, NY (US); Junko Matsuzaki, Williamsville, NY (US); Takemasa Tsuji, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 288 days.

(21) Appl. No.: 14/774,723

(22) PCT Filed: Mar. 13, 2014

(86) PCT No.: PCT/US2014/025673
§ 371 (c)(1),
(2) Date: Sep. 11, 2015

(87) PCT Pub. No.: WO2014/160030
PCT Pub. Date: Oct. 2, 2014

(65) Prior Publication Data
US 2016/0024174 A1 Jan. 28, 2016

Related U.S. Application Data

(60) Provisional application No. 61/778,673, filed on Mar. 13, 2013.

(51) Int. Cl.
| | |
|---|---|
| C12N 15/00 | (2006.01) |
| C07K 14/725 | (2006.01) |
| A61K 39/00 | (2006.01) |
| C12N 5/0783 | (2010.01) |
| C12N 15/85 | (2006.01) |

(52) U.S. Cl.
CPC ...... *C07K 14/7051* (2013.01); *A61K 39/0011* (2013.01); *C12N 5/0636* (2013.01); *C12N 15/85* (2013.01); *A61K 2039/5156* (2013.01); *C07K 2319/00* (2013.01); *C07K 2319/50* (2013.01); *C12N 2740/13041* (2013.01)

(58) Field of Classification Search
None
See application file for complete search history.

(56) References Cited

U.S. PATENT DOCUMENTS

| | | |
|---|---|---|
| 2004/0077601 A1 | 4/2004 | Miller et al. |
| 2004/0253235 A1 | 12/2004 | Kurnick et al. |
| 2010/0021468 A1 | 1/2010 | Wang et al. |
| 2010/0168390 A1 | 7/2010 | Brix et al. |
| 2011/0014169 A1 | 1/2011 | Molloy et al. |
| 2011/0236411 A1 | 9/2011 | Scholler et al. |
| 2011/0318380 A1 | 12/2011 | Scholler et al. |

FOREIGN PATENT DOCUMENTS

| | | |
|---|---|---|
| WO | 200135903 | 5/2001 |
| WO | 2004087941 | 10/2004 |
| WO | 2007131092 | 11/2007 |
| WO | 2010037397 | 4/2010 |
| WO | 2010088160 | 8/2010 |
| WO | 2010106431 | 9/2010 |
| WO | 2011040978 | 4/2011 |
| WO | 2012038055 | 3/2012 |

OTHER PUBLICATIONS

Odunsi et al. (Proc Natl Acad Sci U S A. Jul. 31, 2007;104(31):12837-42 (Year: 2007).*
Hunder et al. (N Engl J Med 2008;358:2698-703) (Year: 2008).*
Li et al. (J Exp Med. Dec. 1, 1991;174(6):1537-47) (Year: 1991).*
Creative Biolabs, datasheet for "Human anti-NY-ESO-1 T cell receptor (5B8), pCDTCR1," retrieved from the internet Dec. 19, 2017, pp. 1-2. (Year: 2017).*
Creative Biolabs, datasheet for "Lenti-NY-ESO-1 T cell receptor (5B8) Viral Particle," retrieved from the internet Dec. 19, 2017, pp. 1- 2. (Year: 2017).*
Robbins et al., Single and Dual Amino Acid Substitutions in TCR CDRs Can Enhance Antigen-Specific T Cell Functions, The Journal of Immunology, 2008, 180:6116-6131. Jan. 1, 2008.
Robbins et al., Tumor Regression in Patients With Metastatic Synovial Cell Sarcoma and Melanoma Using Genetically Engineered Lymphocytes Reactive With NY-ESO-1, J. Clin. Oncol. 29:917-924. Jan. 31, 2011.
GenBank: ACY74602.1, T Cell receptor alpha chain [*Homo sapiens*]. Mar. 1, 2010.

(Continued)

*Primary Examiner* — Zachary S Skelding
(74) *Attorney, Agent, or Firm* — Hodgson Russ LLP

(57) ABSTRACT

Provided are compositions and methods for prophylaxis and/or therapy of a variety of cancers which express a NY-ESO-1 antigen. Included are recombinant T cell receptors (TCRs), polynucleotides encoding them, expression vectors that include the polynucleotides, and cells into which the polynucleotides have been introduced to produce modified cells, including CD4$^+$ T cells, CD8$^+$ T cells, natural killer T cells, γδ T cells, and progenitor cells, such as haematopoietic stem cells. The modified cells are capable of direct recognition of a cancer cell expressing a NY-ESO-1 antigen by human leukocyte antigen (HLA) class II-restricted binding of the TCR to the NY-ESO-1 antigen expressed by the cancer cell without presentation of the antigen by antigen presenting cells. In embodiments, the NY-ESO-1 antigen is displayed by the tumor cells. Also included is a method for prophylaxis and/or therapy of cancer by administering modified cells that express a recombinant TCR. Methods for making expression vectors and/or cells which express a recombinant TCR and identifying TCRs to make the expression vectors are also included.

3 Claims, 4 Drawing Sheets

(56) References Cited

OTHER PUBLICATIONS

GenBank: AAC08958.1, T Cell receptor beta chain [*Homo sapiens*]. Nov. 2, 2001.
GenBank: CAA45055.1, T Cell antigen receptor alpha chain [*Homo sapiens*]. Dec. 6, 1992.
GenBank: ACA28840.1, T Cell receptor variable beta 2 chain [Homo sapiens]. Mar. 1, 2008.
Kronig et al., Allorestricted T lymphocytes with a high avidity T-cell receptor towards NY-ESO-1 have potent anti-tumor activity, International Journal of Cancer, vol. 125, No. 3, pp. 649-655. Aug. 1, 2009.
Zhao et al., Transduction of an HLA-DP4-restricted NY-ESO-1-specific TCR into primary human CD4(+) lymphocytes, Journal of Immunotherapy, vol. 29, No. 4, pp. 398-406. Jul. 1, 2006.
Zhao et al., Primary human lymphocytes transduced with NY-ESO-1 antigen-specific TCR genes recognize and kill diverse human tumor cell lines, The Journal of Immunology, vol. 174, No. 7, pp. 4415-4423. Apr. 1, 2005.

\* cited by examiner (A) Retroviral vector (B) TCR expression cassette (A) JM (B) SB95

COMPOSITIONS AND METHOD FOR USE OF RECOMBINANT T CELL RECEPTORS FOR DIRECT RECOGNITION OF TUMOR ANTIGEN

CROSS REFERENCE TO RELATED APPLICATIONS

This application claims priority to U.S. application No. 61/778,673, filed Mar. 13, 2013, the disclosure of which is incorporated herein by reference.

FIELD

The present disclosure relates generally to immunotherapy and more specifically to recombinant T cell receptors that can impart direct tumor recognition capability to T cells.

BACKGROUND OF THE INVENTION

Tumor antigen-specific $CD4^+$ helper T cells play critical roles in the induction and maintenance of anti-tumor immune responses by providing "CD4-help". Activation of $CD4^+$ T cells at the local tumor sites is believed to help overcome multiple immuno-suppression mechanisms and promote tumor eradication by the immune system. However, because of the frequent lack of functional antigen-presenting cells at the local tumor sites, activation of the $CD4^+$ T cells and therefore the provision of CD4-help at the local tumor site is severely limited. There is accordingly an ongoing and unmet need to provide new compositions and methods such that activation of $CD4^+$ T cells and therefore provision of CD4-help can be achieved.

SUMMARY

The present disclosure provides compositions and methods for prophylaxis and/or therapy of a variety of cancers. In general, the cancers are those which express the well-known the NY-ESO-1 antigen. In embodiments, the disclosure includes recombinant T cell receptors (TCRs), polynucleotides encoding them, expression vectors comprising the polynucleotides, cells into which the polynucleotides have been introduced, including but not necessarily limited $CD4^+$ T cells, $CD8^+$ T cells, natural killer T cells, γδ T cells, and progenitor cells, such as haematopoietic stem cells. In embodiments, the cells into which the polynucleotides are introduced are lymphoid progenitor cells, immature thymocytes (double-negative CD4–CD8–) cells, or double-positive thymocytes (CD4+CD8+). In embodiments, the progenitor cells comprise markers, such as CD34, CD117 (c-kit) and CD90 (Thy-1).

In one aspect the disclosure includes a modified human T cell comprising a recombinant polynucleotide encoding a TCR, wherein the T cell is capable of direct recognition of a cancer cell expressing a NY-ESO-1 antigen, wherein the direct recognition of the cancer cell comprises human leukocyte antigen (HLA) class II-restricted binding of the TCR to the NY-ESO-1 antigen expressed by the cancer cell. In particular embodiments, the TCR encoded by the polynucleotide and expressed by the cell has a TCR alpha chain having the sequence of SEQ ID NO:3 and a TCR beta chain having the sequence of SEQ ID NO:4, or a TCR alpha chain having the sequence of SEQ ID NO:7 and a TCR beta chain having the sequence of SEQ ID NO:8, or a TCR alpha chain having the sequence of SEQ ID NO:11 and a TCR beta chain having the sequence of SEQ ID NO:12. All combination of such alpha and beta chains are included in the disclosure. In an embodiment, the modified cell of claim 1, wherein the sequence encoding the alpha chain and/or the beta chain does not comprise introns. In embodiments, the TCRs of this disclosure include amino acid sequences that are 95%, 96%, 97%, 98%, or 99% amino acid sequence identify across the length of the amino acid sequences disclosed herein.

In another aspect the disclosure includes a method for prophylaxis and/or therapy of an individual diagnosed with, suspected of having or at risk for developing or recurrence of a cancer, wherein the cancer comprises cancer cells which express NY-ESO-1 antigen. This approach comprises administering to the individual modified human T cells comprising a recombinant polynucleotide encoding a TCR, wherein the T cells are capable of direct recognition of the cancer cells expressing the NY-ESO-1 antigen, and wherein the direct recognition of the cancer cells comprises HLA class II-restricted binding of the TCR to the NY-ESO-1 antigen expressed by the cancer cells. In embodiments, the cells comprising the recombinant TCR are human $CD4^+$ T cells. In embodiments, the cells comprising the recombinant TCR that is administered to the individual are allogeneic, syngeneic, or autologous cells. Thus, in one embodiment, the cells are obtained from a first individual, modified, and administered to a second individual who is in need thereof. In another embodiment, the cells are removed from the individual prior, modified to express the recombinant TCR, and administered back to the same individual.

In embodiments, the cancer that expresses the NY-ESO-1 antigen is selected from bladder cancer cells, brain cancer cells, breast cancer cells, gastric cancer cells, esophageal cancer cells, head and neck cancer cells, hepatobiliary cancer cells, kidney cancer cells, ovary cancer cells, non-small cell lung cancer cells, myeloma, prostate cancer cells, sarcoma cells, testicular cancer cells, melanoma cells, and combinations thereof.

In another aspect the disclosure includes one or more expression vectors. The expression vector(s) encode a TCR that is capable of imparting to a cell which expresses it the capability to directly a cancer cell expressing a NY-ESO-1 antigen, wherein the direct recognition of the cancer cell comprises HLA class II-restricted binding of the TCR to the NY-ESO-1 antigen expressed by the cancer cell.

In another approach, methods for making expression vectors and/or cells which express a recombinant TCR. The method involves obtaining a plurality of T cells from an individual, identifying T cells that are capable of direct recognition of a cancer cell displaying a NY-ESO-1 antigen in an HLA class II-restricted manner without antigen presenting cells presenting the NY-ESO-1 antigen to the T cells, determining the sequence of the alpha chain of the TCR and the sequence of the beta chain of the TCR, and introducing into an expression vector a polynucleotide sequence encoding the alpha chain of the TCR and the beta chain of the TCR. In an embodiment, this method comprises introducing the expression vector into a cell such that the TCR is expressed.

DESCRIPTION OF THE INVENTION

The present disclosure relates to immune cells, including but not necessarily limited to T cells, that have been engineered to be capable of direct recognition of tumor antigen and MHC class II-expressing cancer cells. In embodiments, the immune cells are CD4$^+$ T cells, CD8$^+$ T cells, natural killer T cells, γδ T cells, or their progenitor cells such hematopoietic stem/progenitor cells. In embodiments, the hematopoietic/progenitor cells are characterized by one or more markers selected from CD34, CD117 (c-kit) and CD90 (Thy-1).

It is well known that CD4$^+$ T cells typically recognize peptide fragments presented on MHC class II (HLA class II in humans) by antigen presenting cells, such as macrophages and dendritic cells. In addition to antigen-presenting cells, many human cancer cells are also known to express MHC class II constitutively or in an IFN-γ-inducible manner, but the role of MHC class II expression on human cancer cells remains largely unknown.

Figure 1:
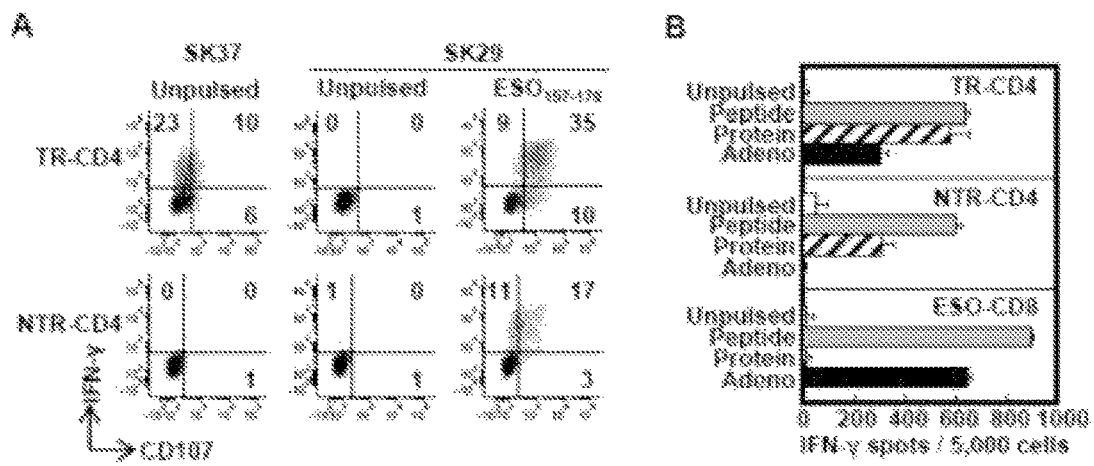
FIG. 1. (A) Direct recognition of cancer cells by JM $CD4^+$ T cell clone. Interferon (IFN)-γ and CD107 expression of NY-ESO-$1_{157-170}$ peptide-specific tumor-recognizing $CD4^+$ T cell clone (Clone: JM) (TR-CD4) and non-tumor-recognizing $CD4^+$ T cell clone (NTR-CD4) after coculture with NY-ESO-1-expressing SK-MEL-37 (SK37) and NY-ESO- 1-negative SK-MEL-29 (SK29) with or without pulsing with the cognate NY-ESO-1$_{157\text{-}170}$ (ESO-1$_{157\text{-}170}$) peptide was investigated by intracellular cytokine staining. (B) Differences in intracellular and extracellular NY-ESO-1 recognition by NY-ESO-1-specific CD4$^+$ and CD8$^+$ T cell clones. NY-ESO-1-negative SK-MEL-29 was unpulsed (Unpulsed) or pulsed with NY-ESO-1$_{157\text{-}170}$ peptide (Peptide) or recombinant NY-ESO-1 protein (Protein), or was infected with adenovirus vector which induce intracellular NY-ESO-1 expression. Recognition by TR-CD4, NTR-CD4 and NY-ESO-1-specific CD8$^+$ T cell clone was evaluated by IFN-γ ELISPOT assay.

We have now discovered that there are two distinct types of tumor antigen-specific CD4$^+$ T cells. One type of tumor antigen-specific CD4$^+$ T cells is referred to herein as tumor-recognizing CD4$^+$ T cells (TR-CD4). This type of CD4$^+$ T cell directly recognizes MHC (HLA in humans) class II-expressing cancer cells in antigen-specific and MHC class II-restricted manner. In contrast, another type of previously known, antigen-specific CD4$^+$ T cells is referred to herein as non-tumor-recognizing CD4$^+$ T cells (NTR-CD4). This type of T cell only recognizes exogenous tumor antigen peptides after processing by antigen-presenting cells. FIGS. 1A and 1B depict data demonstrating these distinct functions and reveal direct recognition of cancer cells by TR-CD4.

Because of their different abilities in direct recognition of cancer cells, these two types of CD4$^+$ T cells (TR-CD4 and NTR-CD4) are believed to play different roles at the local tumor site. Without intending to be constrained by any particular theory, it is believed that TR-CD4 cells provide CD4-help by direct recognition of cancer cells. The present invention takes advantage of this function to provide TCR polypeptides and recombinant polynucleotides encoding them for use in novel prophylactic and/or therapeutic treatment modalities and compositions. By engineering T cells to express the TCRs further described herein, we can endow any CD4$^+$ cell with the capability to directly recognize tumor antigen-expressing cancer cells, without requiring presentation of the antigen by an antigen-presenting cell. Thus, the present invention includes compositions and methods that are useful for creating and using TR-CD4 cells for improved care of cancer patients.

Previous attempts at making and using recombinant TCRs have been made. For example, U.S. Pat. No. 8,008,438 (the '438 patent) discloses recombinant TCRs which bind to the peptide sequence SLLMWITQC from the NY-ESO-1 protein (NY-ESO-1:157-165). However, and importantly, the disclosure in the '438 patent pertains to classic CD8$^+$ TCRs, which only recognize the NY-ESO-1:157-165 peptide in the context of the HLA-A*0201 class I restriction element. This constitutes a significant dissimilarity from the present invention because, as described above, the recombinant TCRs of the present invention are class II restricted. Moreover, and as also described above, unlike canonical class II restriction, cells engineered to express a recombinant TCR of the invention surprisingly do not require the assistance of antigen presenting cells to recognize the antigens to which they are specific. Instead, they can recognize the antigens as they exist in vivo as a peptide displayed by the tumor cells. Further, the TCRs of the present invention recognize peptides by those disclosed in the '438 patent. Accordingly, the present invention is a significant and unexpected departure from the prior art. In an embodiment, a TR-CD4 is a CD4+ cell that exhibits cytokine secretion (such as IFN-gamma production) when the TR-CD4 is directly exposed to cells which express an antigen for which the TCR is specific in an HLA-II context. The ability to confer capability for direct recognition of NY-ESO-1-expressing tumors by CD4+ T cells by introducing a TCR from a naturally occurring cell having this capability was unexpected.

In one embodiment, the invention includes transforming any CD4$^+$ T cell into a TR-CD4 by introducing a polynucleotide encoding a recombinant TCR of the invention into polyclonally expanded CD4$^+$ T cells and allowing expression of the TCR polypeptide coding region(s) of the polynucleotide.

In various embodiments, the present invention provides isolated and/or recombinant polynucleotides encoding particular TCR polypeptides, cells engineered to express the TCR polypeptides, pharmaceutical formulations comprising cells which express the TCR polypeptides, and methods of using the pharmaceutical formulations to achieve a prophylactic and/or therapeutic effect against cancer in a subject. In certain embodiments, the invention provides mixtures of cells expressing TCRs, or cells expressing more than one TCR described herein, that are specific for distinct cancer antigens, thus presenting cell populations that can be considered polyvalent with respect to the TCRs. As used in this disclosure, a "recombinant TCR" means a TCR that is expressed from a polynucleotide that was introduced into the cell, meaning prior to the introduction of the polynucleotide the TCR was not encoded by a chromosomal sequence in the cell.

The TCRs provided by the invention are capable of recognizing NY-ESO-1;157-170 which is an antigen that consists of the amino acid sequence SLLMWITQCFLPVF, or are capable of recognizing NY-ESO-1;95-106, which is an antigen that consists of the amino acid sequence PFATPMEAELAR. As described above, in certain embodiments, the cells provided by the invention are engineered CD4$^+$ T cells that are capable of recognizing these antigens via TCRs which interact with the antigen in association with HLA class II molecules, wherein the HLA class II molecules and antigen are displayed by tumor cells.

The invention includes each and every polynucleotide sequence that encodes one or more TCR polypeptides of the invention and disclosed herein, including DNA and RNA sequences, and including isolated and/or recombinant polynucleotides comprising and/or consisting of such sequences. The invention also includes cells which comprise the recombinant polynucleotides. The cells can be isolated cells, cells grown and/or expanded and/or maintained in culture, and can be prokaryotic or eukaryotic cells. Prokaryotic and eukaryotic cell cultures can be used, for example, to propagate or amplify the TCR expression vectors of the invention. In embodiments, the cells can comprise packaging plasmids, which, for example, provide some or all of the proteins used for transcription and packaging of an RNA copy of the expression construct into recombinant viral particles, such as pseudoviral particles. In embodiments, the expression vectors are transiently or stably introduced into cells. In embodiments, the expression vectors are integrated into the chromosome of cells used for their production. In embodiments, polynucleotides encoding the TCRs which are introduced into cells by way of an expression vector, such as a viral particle, are integrated into one or more chromosomes of the cells. Such cells can be used for propagation, or they can be cells that are used for therapeutic and/or prophylactic approaches. The eukaryotic cells include CD4$^+$ T cells, CD8$^+$ T cells, natural killer T cells, γδ T cells, and their progenitor cells into which a TCR expression construct of the invention has been introduced. The CD4$^+$ T cells can be from any source, including but not limited to a human subject who may or may not be the eventual recipient of the CD4$^+$ T cells once they have been engineered to express a TCR according to the invention.

Expression vectors for use with embodiments of this disclosure can be any suitable expression vector. In embodiments, the expression vector comprises a modified viral polynucleotide, such as from an adenovirus, a herpesvirus, or a retrovirus, such as a lentiviral vector. The expression vector is not restricted to recombinant viruses and includes non-viral vectors such as DNA plasmids and in vitro transcribed mRNA.

With respect to the polypeptides that are encoded by the polynucleotides described above, in certain aspects the invention provides functional TCRs which comprises a TCR α and a TCR β chain, wherein the two chains are present in a physical association with one another (e.g., in a complex) and are non-covalently joined to one another, or wherein the two chains are distinct polypeptides but are covalently joined to one another, such as by a disulfide or other covalent linkage that is not a peptide bond. Other suitable linkages can comprise, for example, substituted or unsubstituted polyalkylene glycol, and combinations of ethylene glycol and propylene glycol in the form of, for example, copolymers. In other embodiments, two polypeptides that constitute the TCR α and a TCR β chain can both be included in a single polypeptide, such as a fusion protein. In certain embodiments, the fusion protein comprises a TCR α chain amino acid sequence and a TCR β chain amino acid sequence that have been translated from the same open reading frame (ORF), or distinct ORFs, or an ORF that contain a signal that results in non-continuous translation. In one embodiment, the ORF comprises a P2A-mediated translation skipping site positioned between the TCR α and TCR β chain. Constructs for making P2A containing proteins (also referred to as 2A Peptide-Linked multicistronic vectors) are known in the art. (See, for example, *Gene Transfer: Delivery and Expression of DNA and RNA, A Laboratory Manual*, (2007), Friedman et al., International Standard Book Number (ISBN) 978-087969765-5. Briefly, 2A peptide sequences, when included between coding regions, allow for stoichiometric production of discrete protein products within a single vector through a novel cleavage event that occurs in the 2A peptide sequence. 2A peptide sequences are generally short sequence comprising 18-22 amino acids and can comprise distinct amino-terminal sequences. Thus, in one embodiment, a fusion protein of the invention includes a P2A amino acid sequence. In embodiments, a fusion protein of the invention can comprise a linker sequence between the TCR α and TCR β chains. In certain embodiments, the linker sequence can comprise a GSG (Gly-Ser-Gly) linker or an SGSG (Ser-Gly-Ser-Gly) linker. In certain embodiments, the TCR α and TCR β chains are connected to one another by an amino acid sequence that comprises a furin protease recognition site, such as an RAKR (Arg-Ala-Lys-Arg) site.

In one embodiment, the expression construct that encodes the TCR can also encode additional polynucleotides. The additional polynucleotide can be such that it enables identification of TCR expressing cells, such as by encoding a detectable marker, such as a fluorescent or luminescent protein. The additional polynucleotide can be such that it encodes an element that allows for selective elimination of TCR expressing cells, such as thymidine kinase gene. In embodiments the additional polynucleotides can be such that they facilitate inhibition of expression of endogenously encoded TCRs. In an embodiment, the expression construct that encodes the TCR also encodes a polynucleotide which can facilitate RNAi-mediated down-regulation of one or more endogenous TCRs For example, see Okamoto S, et al. (2009) Cancer Research, 69:9003-9011, and Okamoto S, et al. (2012). Molecular Therapy-Nucleic Acids, 1, e63. In an embodiment, the expression construct that encodes the TCR can encode an shRNA or an siRNA targeted to an endogenously encoded TCR. In an alternative embodiment, a second, distinct expression construct that encodes the polynucleotide for use in downregulating endogenous TCR production can be used.

Figure 6:
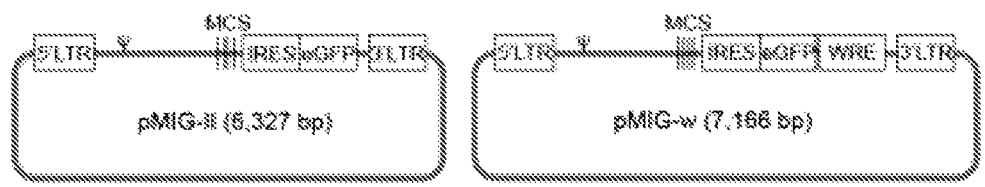
FIG. 6. (A) Retrovirus vector used in the experiments. LTR: long-terminal repeat; ψ: packaging signal; MCS: multiple cloning site; IRES: internal ribosome entry site; eGFP: enhanced green fluorescent protein. (B) TCR expressing cassette. (I) TCR β and α chain-coding cDNA sequences are connected by a GSG (Gly-Ser-Gly) linker and a P2A ribosomal skipping sequence. (II) TCR β and α chain-coding cDNA sequences are connected by a furin protease recognition site (RAKR (Arg-Ala-Lys-Arg)), a SGSG (Ser-Gly-Ser-Gly) linker, V5 epitope, and a P2A ribosomal skipping sequence.
Figure 6:
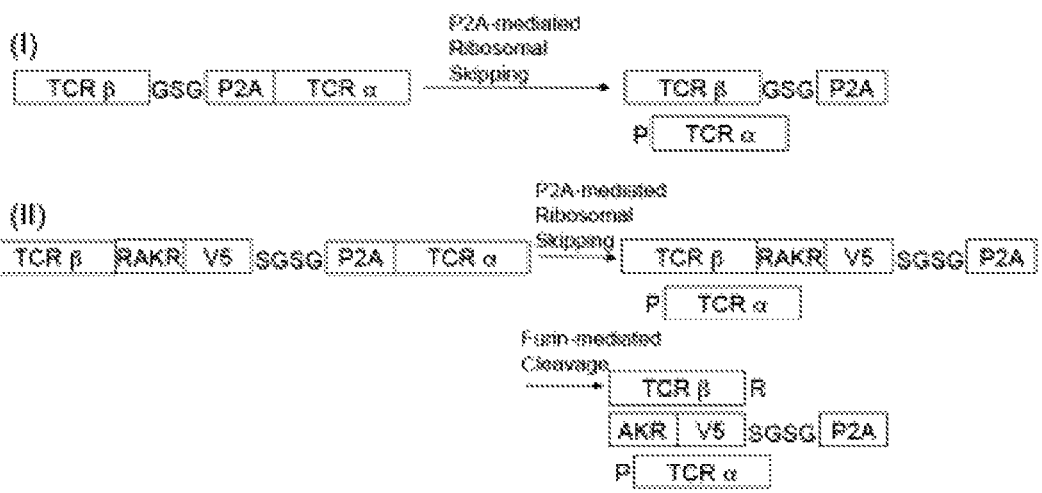

FIG. 6 provides representative configurations of TCR polypeptides of the invention and polynucleotides/expression vectors encoding them. In one embodiment, as outlined in FIG. 6, an amino acid sequence that is C-terminal to the TCR β chain protein is removed by furin protease-mediated cleavage, resulting in functional TCR α and β chain proteins. It will be also recognized from FIG. 6 that the TCR chains can be expressed from an expression construct such that the β chain is oriented N-terminally in relation to the α chain, and thus TCRs of the invention can also comprise this chain orientation, or other orientations. In alternative embodiments, the TCR α and β chain proteins can be expressed from distinct expression vectors introduced into the same cell.

In connection with the present invention, we have also made the following discoveries: in certain instances, intracellular tumor antigen is loaded on HLA class II through recycling of the HLA class II in tumors; direct tumor recognition by tumor-recognizing CD4$^+$ T cells leads to in vivo tumor growth inhibition; CD4$^+$ T cells efficiently augment CD8$^+$ T cell cytotoxicity through direct tumor recognition; CD4$^+$ T cells support proliferation, survival, and memory differentiation of cognate antigen-specific CD8$^+$ T cells through direct tumor recognition without antigen presenting cells. It is expected that practicing the present invention in a clinical setting will also result in direct tumor recognition by the engineered tumor-recognizing CD4$^+$ T cells and lead to in vivo tumor growth inhibition in human subject, and will also result in the efficient augmentation of CD8$^+$ T cell cytotoxicity by the engineered CD4$^+$ T cells, and that the engineered CD4$^+$ T cells will support proliferation, survival, and memory differentiation of cognate antigen-specific CD8$^+$ T cells in human subjects who receive CD4$^+$ T cells engineered according to the invention.

With respect to use of the engineered CD4$^+$ T cells of the present invention, the method generally comprises administering an effective amount (typically $10^{10}$ cells by intravenous or intraperitoneal injections) of a composition comprising the CD4$^+$ T cells to an individual in need thereof. An individual in need thereof, in various embodiments, is an individual who has or is suspected of having, or is at risk for developing a cancer which is characterized by malignant cells that express NY-ESO-I. As is well known in the art, NY-ESO-I is expressed by a variety of cancer cells and tumor types. In particular and non-limiting examples, such cancers include cancers of the bladder, brain, breast, ovary, non-small cell lung cancer, myeloma, prostate, sarcoma and melanoma. Specific embodiments include but are not limited to liposarcomas and intrahepatic cholagiocarcinoma. The individual may have early-stage or advanced forms of any of these cancers, or may be in remission from any of these cancers. In one embodiment, the individual to whom a composition of the invention is administered is at risk for recurrence for any cancer type that expresses NY-ESO-1. In certain embodiments, the individual has or is suspected of having, or is at risk for developing or recurrence of a tumor comprising cells which express a protein comprising the amino acid sequences defined by NY-ESO-1:157-170 and/or NY-ESO-1:95-106. In embodiments, the disclosure includes recombinant TCRs that are specific for peptide fragments of NY-ESO-1 that are between 15 and 24 amino acid residues long, wherein such peptides are presented in a complex with HLA-II. In embodiments, the disclosure includes recombinant TCRs that are specific for peptides that are in a complex with HLA-II, wherein the peptides comprise or consist of the amino acid sequences of NY-ESO-1:157-170 and/or NY-ESO-1:95-106.

The present disclosure includes recombinant TCRs, cells expressing them, and therapeutic/prophylactic methods that involve presentation of NY-ESO-1 antigens in conjunction with any HLA-class II complex that will be recognized by the TCRs. In embodiments, the HLA-II is selected from HLA-DP, HLA-DQ, and HLA-DR. In embodiments, the NY-ESO-1 antigen is recognized by the TCR in conjunction with HLA-DRB1*01 or HLA-DPB1*04.

Figure 2:
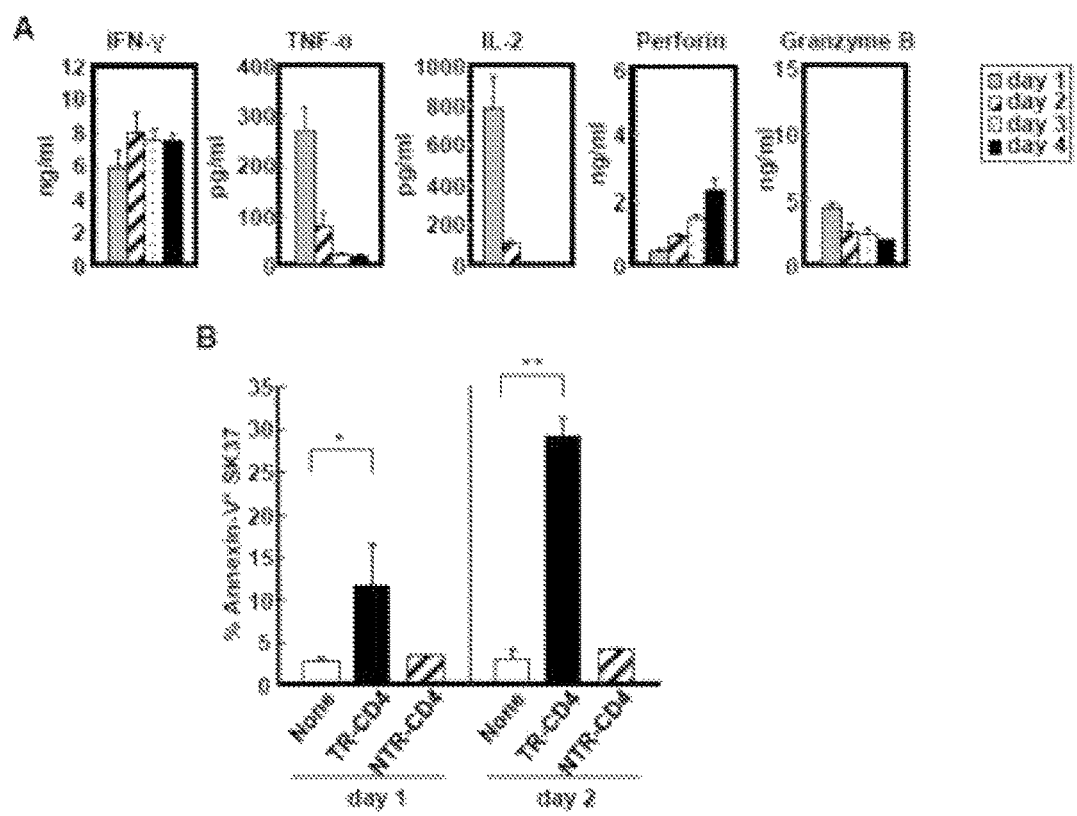
FIG. 2. (A) TR-CD4 (Clone: JM) were co-cultured with SK-MEL-37. Culture supernatant was harvested after 1-4 days of culture. The levels of the indicated cytokines and lytic molecules in the supernatant were measured by ELISA. (B) TR-CD4 and NTR-CD4 was co-cultured with SK-MEL-37 and expression of the early apoptosis marker, Annexin-V, on SK-MEL-37 (SK37) was measured by flow-cytometry.
Figure 3:
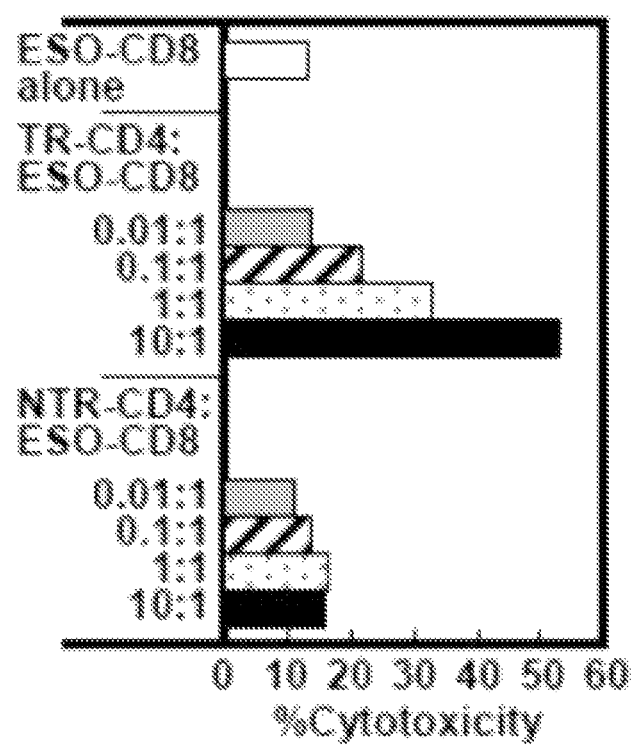
FIG. 3. NY-ESO-1-specific CD8$^+$ T cell clone (ESO-CD8) was co-cultured with SK-MEL-37 at 1:2 ratio in the presence or absence of the indicated ratios of TR-CD4 (Clone: JM). Cytotoxic activity by ESO-CD8 on SK-MEL-37 was evaluated by CFSE-based cytotoxicity assay.
Figure 4:
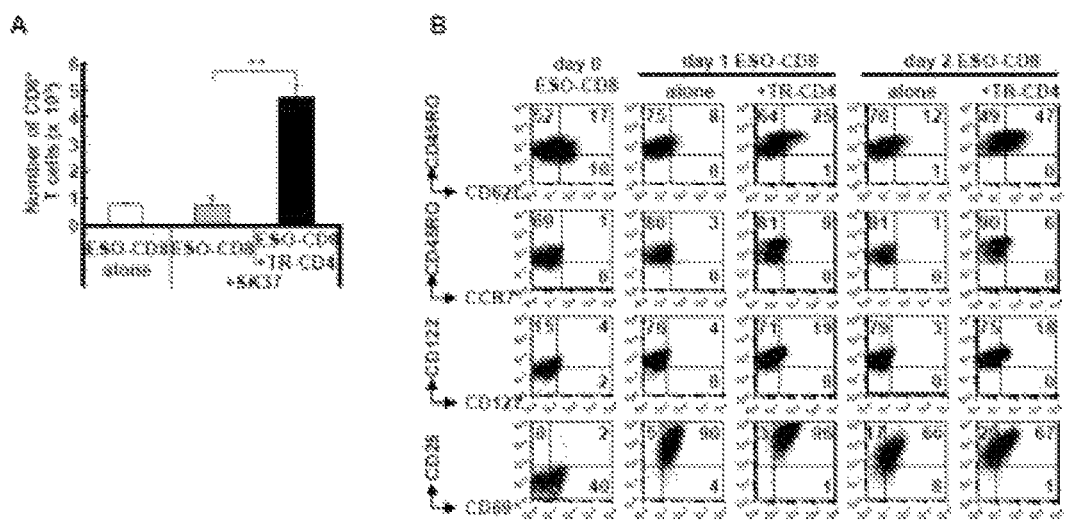
FIG. 4. (A) NY-ESO-1-specific CD8$^+$ T cell clone (ESO-CD8) was stimulated with or without SK-MEL-37 (SK37) in the presence or absence of TR-CD4 (clone: JM). After 4 days, the number of CD8$^+$ T cells were enumerated by trypan blue exclusion assay combined with CD8 staining by flow-cytometry. (B) ESO-CD8 was stimulated with SK37 in the presence or absence of TR-CD4. Before (day 0) and after (day 1 and day 2) stimulation, expression of activation markers (CD25, CD69 and CD122) or central T cell differentiation markers (CD62L, CCR7 and CD127) on ESO-CD8 was measured by flow-cytometry.

We demonstrate in this invention that TR-CD4 we created produce multiple molecules through direct recognition of cancer cells, which induced apoptosis in cancer cells (FIGS. 2A and 2B) Importantly, TR-CD4 were found to efficiently enhance the cytotoxic activity of tumor antigen-specific CD8$^+$ T cells via direct recognition of cancer cells in the absence of antigen-presenting cells (FIG. 3). Furthermore, CD8$^+$ T cells co-stimulated with TR-CD4 by cancer cells actively proliferated and upregulated central memory T cell markers (FIGS. 4A and 4B).

Figure 5:
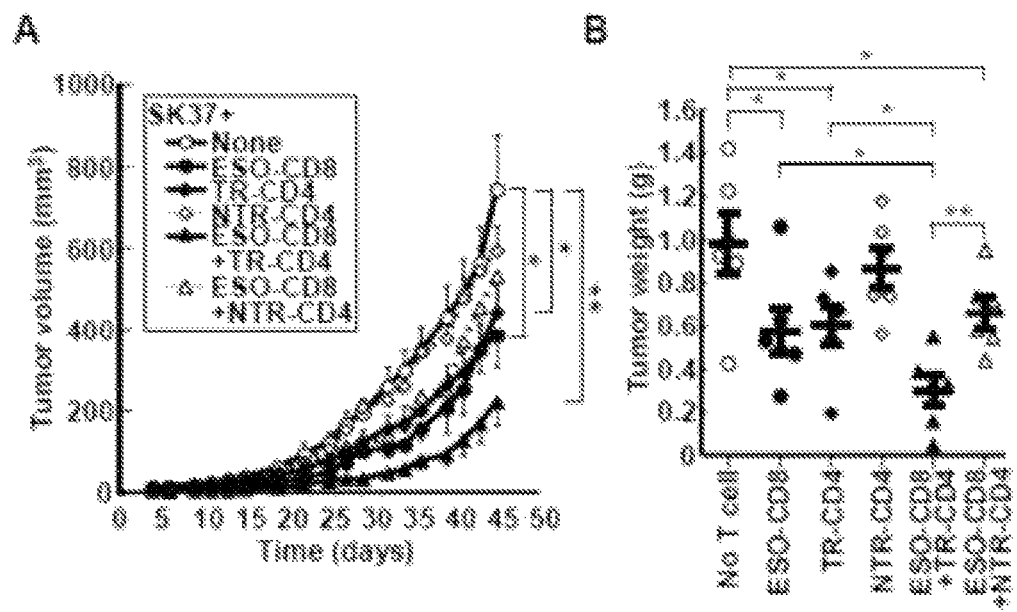
FIG. 5. (A) SK-MEL-37 was inoculated in SCID mice (6 mice/group) with or without tumor-recognizing CD4$^+$ T cell clone (JM: TR-CD4), non-tumor-recognizing CD4$^+$ T cell clone (NTR-CD4), and/or NY-ESO-1-specific CD8$^+$ T cell clone (ESO-CD8). Tumor growth was measured every 2-3 day. (B) Tumor was excised and weighted at day 45 after inoculation.

TR-CD4 showed significant in vivo anti-tumor activity to inhibit the growth of human cancer cells in immuno-deficient mice (FIG. 5). In addition, TR-CD4 and tumor antigen-specific CD8$^+$ T cells co-operatively inhibited in vivo tumor growth (FIG. 5). Thus, the data presented herein strongly suggest that the recruitment of TR-CD4 at the local tumor site potentiate the anti-tumor immune responses, and accordingly will likely make an effective and heretofore unavailable therapeutic approach for widespread use in the clinic.

The following description provides illustrative examples of materials and methods used to make and use various embodiments of the invention.

To develop a method to efficiently generate a large number of TR-CD4 by gene-engineering with tumor-recognizing T cell receptor (TCR) gene, full length TCR gene from three TR-CD4 clones were cloned and sequenced by using 5'-RACE-PCR technique. The following TCRs were created:

1. HLA-DRB1*01-restricted NY-ESO-1:96-106-specific TR-CD4 (referred to herein as Clone: "SB95")
2. HLA-DPB1*04-restricted NY-ESO-1:157-170-specific TR-CD4 (referred to herein as Clone: "5B8")
3. HLA-DPB1*04-restricted NY-ESO-1:157-170-specific TR-CD4 (referred to herein as Clone: "JM")

TCR genes from SB95 and JM were inserted into retroviral expression vectors (such as MSCV-derived pMIG-II or pMIG-w vectors). A 5B8 TCR-expressing vector is made in the same manner.

Retroviral transduction of these TCR genes efficiently transferred reactivity against cognate peptides to polyclonally expanded T cells from peripheral blood mononuclear cells (PBMC) from healthy individuals. The nucleotide and amino acid sequences presented below represent those used to demonstrate the invention. The invention includes any and all polynucleotide sequences encoding the amino acid sequences of the TCR constructs described herein.

Further, variations in amino acid sequences in the TCRs are contemplated, so long as they do not adversely affect the function of the TCR. In various embodiments, a TCR comprising one or more amino acid changes as compared to the sequences presented herein will comprise conservative amino acid substitutions or other substitutions, additions or deletions, so long as the cells expressing the recombinant TCRs of the invention can directly and specifically recognize tumor cells that express NY-ESO-1, wherein that recognition is dependent on expression of NY-ESO-1 and presentation of peptides processed from it in an HLA class II restricted manner by the tumor cells. In embodiments, a TCR of the present invention comprises any amino acid sequence that facilitates direct recognition of the tumor antigen on the tumor cells, without participation of an antigen presenting cells. In embodiments, the amino acid sequence of a TCR provided by this disclosure is at least 95%, 96%, 97%, 98% or 99% similar to an amino acid sequences provided in the sequence listing that is part of this disclosure. In various embodiments, any TCR of the invention can have a $K_{off}$ value for its cognate epitope as defined herein that is essentially the same as the $K_{off}$ for the cognate epitope exhibited by a TCR of a naturally occurring TR-CD4 for the same epitope. In embodiments, the TCR amino acid sequences can comprise changes in their constant region. In this regard, it is known in the art that in general, the constant region of a TCR does not substantially contribute to antigen recognition. For example, it is possible to replace a portion of the human constant region of a TCR with a murine sequence and retain function of the TCR. (See, for example, Goff S L et al. (2010) Cancer Immunology, Immunotherapy, 59: 1551-1560). Thus, various modifications to the TCR sequences disclosed herein are contemplated, and can include but are not limited to changes that improve specific chain pairing, or facilitate stronger association with T cell signaling proteins of the CD3 complex, or inhibit formation of dimers between the endogenous and introduced TCRs. In embodiments, the amino acid changes can be present in the CDR region, such as the CDR3 region, including but not necessarily limited to substitutions of one, two, three, or more amino acids in the CDR3 sequence. In embodiments, the amino acid changes have no effect on the function of the TCR.

In specific and illustrative embodiments, the polynucleotide sequences encoding the TCRs of the invention, and the amino acid sequences of the TCR α and TCR β chains encoded by the polynucleotides are as follows, wherein translation initiation and stop codons in the polynucleotide sequences are bold:

"JM" HLA-DPB1 *0401/0402-restricted NY-ESO-1$_{157-170}$-specific tumor-recognizing CD4⁺ T cell clone
(a) cDNA nucleotide sequences of TCR α and β chains
TCR α chain (SEQ ID NO: 1)

ATGAAGTTGGTGACAAGCATTACTGTACTCCTATCTTTGGGTATTATGGGTGATGCTAAGAC

CACACAGCCAAATTCAATGGAGAGTAACGAAGAAGAGCCTGTTCACTTGCCTTGTAACCAC

TCCACAATCAGTGGAACTGATTACATACATTGGTATCGACAGCTTCCCTCCCAGGGTCCAGA

GTACGTGATTCATGGTCTTACAAGCAATGTGAACAACAGAATGGCCTCTCTGGCAATCGCTG

AAGACAGAAAGTCCAGTACCTTGATCCTGCACCGTGCTACCTTGAGAGATGCTGCTGTGTAC

TACTGCATCCCTAATAACAATGACATGCGCTTTGGAGCAGGGACCAGACTGACAGTAAAAC

CAAATATCCAGAACCCTGACCCTGCCGTGTACCAGCTGAGAGACTCTAAATCCAGTGACAA

GTCTGTCTGCCTATTCACCGATTTTGATTCTCAAACAAATGTGTCACAAAGTAAGGATTCTG

ATGTGTATATCACAGACAAAACTGTGCTAGACATGAGGTCTATGGACTTCAAGAGCAACAG

TGCTGTGGCCTGGAGCAACAAATCTGACTTTGCATGTGCAAACGCCTTCAACAACAGCATTA

TTCCAGAAGACACCTTCTTCCCCAGCCCAGAAAGTTCCTGTGATGTCAAGCTGGTCGAGAAA

AGCTTTGAAACAGATACGAACCTAAACTTTCAAAACCTGTCAGTGATTGGGTTCCGAATCCT

CCTCCTGAAAGTGGCCGGGTTTAATCTGCTCATGACGCTGCGGCTGTGGTCCAGCTGA

TCR β chain (SEQ ID NO: 2)

ATGGGCTCCAGGCTGCTCTGTTGGGTGCTGCTTTGTCTCCTGGGAGCAGGCCCAGTAAAGGC

TGGAGTCACTCAAACTCCAAGATATCTGATCAAAACGAGAGGACAGCAAGTGACACTGAGC

TGCTCCCCTATCTCTGGGCATAGGAGTGTATCCTGGTACCAACAGACCCCAGGACAGGGCCT

TCAGTTCCTCTTTGAATACTTCAGTGAGACACAGAGAAACAAAGGAAACTTCCCTGGTCGAT

TCTCAGGGCGCCAGTTCTCTAACTCTCGCTCTGAGATGAATGTGAGCACCTTGGAGCTGGGG

GACTCGGCCCTTTATCTTTGCGCCAGCAGCTTCCCCAGGGAACCTAACTATGGCTACACCTT

CGGTTCGGGGACCAGGTTAACCGTTGTAGAGGACCTGAACAAGGTGTTCCCACCCGAGGTC

GCTGTGTTTGAGCCATCAGAAGCAGAGATCTCCCACACCCAAAAGGCCACACTGGTGTGCC

-continued

```
TGGCCACAGGCTTCTTCCCTGACCACGTGGAGCTGAGCTGGTGGGTGAATGGGAAGGAGGT

GCACAGTGGGGTCAGCACGGACCCGCAGCCCCTCAAGGAGCAGCCCGCCCTCAATGACTCC

AGATACTGCCTGAGCAGCCGCCTGAGGGTCTCGGCCACCTTCTGGCAGAACCCCCGCAACC

ACTTCCGCTGTCAAGTCCAGTTCTACGGGCTCTCGGAGAATGACGAGTGGACCCAGGATAG

GGCCAAACCCGTCACCCAGATCGTCAGCGCCGAGGCCTGGGGTAGAGCAGACTGTGGCTTT

ACCTCGGTGTCCTACCAGCAAGGGGTCCTGTCTGCCACCATCCTCTATGAGATCCTGCTAGG

GAAGGCCACCCTGTATGCTGTGCTGGTCAGCGCCCTTGTGTTGATGGCCATGGTCAAGAGAA

AGGATTTCTGA
```

(b) amino acid sequences of TCR α and β chains (TCR variable
regions are in italic, CDR3 regions are in bold)
TCR α chain

```
                                                (SEQ ID NO: 3)
MKLVTSTTVLLSLGIMGDAKTTQPNSMESNEEEPVHLPCNHSTISGTDYI       50

HWYRQLPSQGPEYVIHGLTSNVNNRMASLAIAEDRKSSTLILHRATLRDA      100

AVYYCIPNNNDMRFGAGTRLTVKPNIQNPDPAVYQLRDSKSSDKSVCLFT      150

DFDSQTNVSQSKDSDVYITDKTVLDMRSMDFKSNSAVAWSNKSDFACANA      200

FNNSIIPEDTFFPSPESSCDVKLVEKSFETDTNLNFQNLSVIGFRILLLK      250

VAGFNLLMTLRLWSS
```

TCR β chain

```
                                                (SEQ ID NO: 4)
MGSRLLCWVLLCLLGAGPVKAGVTQTPRYLIKTRGQQVTLSCSPISGHRS       50

VSWYQQTPGQGLQFLFEYFSETQRNKGNFPGRFSGRQFSNSRSEMNVSTL      100

ELGDSALYLCASSFPREPNYGYTFGSGTRLTVVEDLNKVFPPEVAVFEPS      150

EAEISHTQKATLVCLATGFFPDHVELSWWVNGKEVHSGVSTDPQPLKEQP      200

ALNDSRYCLSSRLRVSATFWQNPRNHFRCQVQFYGLSENDEWTQDRAKPV      250

TQIVSAEAWGRADCGFTSVSYQQGVLSATILYEILLGKATLYAVLVSALV      300

LMAMVKRKDF
```

"5B8" HLA-DPB1 *0401/0402-restricted NY-ESO-1$_{157-170}$-specific
tumor-recognizing CD4$^+$ T cell clone
(a) cDNA nucleotide sequences of TCR α and β chains
TCR α chain

```
                                                (SEQ ID NO: 5)
ATGGCCCAGACAGTCACTCAGTCTCAACCAGAGATGTCTGTGCAGGAGGCAGAGACTGTGA

CCCTGAGTTGCACATATGACACCAGTGAGAATAATTATTATTTGTTCTGGTACAAGCAGCCT

CCCAGCAGGCAGATGATTCTCGTTATTCGCCAAGAAGCTTATAAGCAACAGAATGCAACGG

AGAATCGTTTCTCTGTGAACTTCCAGAAAGCAGCCAAATCCTTCAGTCTCAAGATCTCAGAC

TCACAGCTGGGGACACTGCGATGTATTTCTGTGCTTTCTCGAGAGGGAGTGGAGGTAGCA

ACTATAAACTGACATTTGGAAAAGGAACTCTCTTAACCGTGAATCCAAATATCCAGAACCCT

GACCCTGCCGTGTACCAGCTGAGAGACTCTAAATCCAGTGACAAGTCTGTCTGCCTATTCAC

CGATTTTGATTCTCAAACAAATGTGTCACAAAGTAAGGATTCTGATGTGTATATCACAGACA

AAACTGTGCTAGACATGAGGTCTATGGACTTCAAGAGCAACAGTGCTGTGGCCTGGAGCAA

CAAATCTGACTTTGCATGTGCAAACGCCTTCAACAACAGCATTATTCCAGAAGACACCTTCT
```

-continued

TCCCCAGCCCAGAAAGTTCCTGTGATGTCAAGCTGGTCGAGAAAAGCTTTGAAACAGATAC

GAACCTAAACTTTCAAAACCTGTCAGTGATTGGGTTCCGAATCCTCCTCCTGAAAGTGGCCG

GGTTTAATCTGCTCATGACGCTGCGGCTGTGGTCCAGCTGA

TCR β chain
(SEQ ID NO: 6)

ATGGGCACCAGGCTCCTCTTCTGGGTGGCCTTCTGTCTCCTGGGGGCAGATCACACAGGAGC

TGGAGTCTCCCAGTCCCCCAGTAACAAGGTCACAGAGAAGGGAAAGGATGTAGAGCTCAGG

TGTGATCCAATTTCAGGTCATACTGCCCTTTACTGGTACCGACAGAGCCTGGGGCAGGGCCT

GGAGTTTTTAATTTACTTCCAAGGCAACAGTGCACCAGACAAATCAGGGCTGCCCAGTGATC

GCTTCTCTGCAGAGAGGACTGGGGGATCCGTCTCCACTCTGACGATCCAGCGCACACAGCA

GGAGGACTCGGCCGTGTATCTCTGTGCCAGCAGCTTAGTCCCCGACAGTGCCTACGAGCAGT

ACTTCGGGCCGGGCACCAGGCTCACGGTCACAGAGGACCTGAAAAACGTGTTCCCACCCGA

GGTCGCTGTGTTTGAGCCATCAGAAGCAGAGATCTCCCACACCCAAAAGGCCACACTGGTA

TGCCTGGCCACAGGCTTCTACCCCGACCACGTGGAGCTGAGCTGGTGGGTGAATGGGAAGG

AGGTGCACAGTGGGGTCAGCACGGACCCGCAGCCCCTCAAGGAGCAGCCCGCCCTCAATGA

CTCCAGATACTGCCTGAGCAGCCGCCTGAGGGTCTCGGCCACCTTCTGGCAGAACCCCCGCA

ACCACTTCCGCTGTCAAGTCCAGTTCTACGGGCTCTCGGAGAATGACGAGTGGACCCAGGAT

AGGGCCAAACCTGTCACCCAGATCGTCAGCGCCGAGGCCTGGGGTAGAGCAGACTGTGGCT

TCACCTCCGAGTCTTACCAGCAAGGGGTCCTGTCTGCCACCATCCTCTATGAGATCTTGCTA

GGGAAGGCCACCTTGTATGCCGTGCTGGTCAGTGCCCTCGTGCTGATGGCCATGGTCAAGAG

AAAGGATTCCAGAGGCTAG

(b) amino acid sequences of TCR α and β chains (TCR variable regions are in italic, CDR3 regions are in bold)
TCR α chain
(SEQ ID NO: 7)

*MAQTVTQSQPEMSVQEAETVTLSCTYDTSENNYYLFWYKQPPSRQMILVI* 50

*RQEAYKQQNATENRFSVNFQKAAKSFSLKISDSQLGDTAMYF*CAFSRGSG 100

GSNYKLT*FGKGTLLTVNPNIQNPDPAVYQLRDSKSSDKSVCLFTDFDSQT 150

NVSQSKDSDVYITDKTVLDMRSMDFKSNSAVAWSNKSDFACANAFNNSII 200

PEDTFFPSPESSCDVKLVEKSFETDTNLNFQNLSVIGFRILLLLKVAGFNL 250

LMTLRLWSS

TCR β chain
(SEQ ID NO: 8)

*MGTRLLFWVAFCLLGADHTGAGVSQSPSNKVTEKGKDVELRCDPISGHTA* 50

*LYWYRQSLGQGLEFLIYFQGNSAPDKSGLPSDRFSAERTGGSVSTLTIQR* 100

*TQQEDSAVYL*CASSLVPDSAYEQYF*GPGTRLTVT*EDLKNVFPPEVAVFEP 150

SEAEISHTQKATLVCLATGFYPDHVELSWWVNGKEVHSGVSTDPQPLKEQ 200

PALNDSRYCLSSRLRVSATFWQNPRNHFRCQVQFYGLSENDEWTQDRAKP 250

VTQIVSAEAWGRADCGFTSESYQQGVLSATILYEILLGKATLYAVLVSAL 300

VLMAMVKRKDSRG

-continued

"SB95" HLA-DRB1*0101-restricted NY-ESO-1$_{95-106}$-specific tumor-recognizing CD4$^+$ T cell clone
(a) cDNA nucleotide sequences of TCR α and β chains
TCR alpha (SEQ ID NO: 9)

ATGCTCCTGCTGCTCGTCCCAGTGCTCGAGGTGATTTTTACCCTGGGAGGAACCAGAGCCCA

GTCGGTGACCCAGCTTGGCAGCCACGTCTCTGTCTCTGAGGGAGCCCTGGTTCTGCTGAGGT

GCAACTACTCATCGTCTGTTCCACCATATCTCTTCTGGTATGTGCAATACCCCAACCAAGGA

CTCCAGCTTCTCCTGAAGCACACAACAGGGGCCACCCTGGTTAAAGGCATCAACGGTTTTGA

GGCTGAATTTAAGAAGAGTGAAACCTCCTTCCACCTGACGAAACCCTCAGCCCATATGAGC

GACGCGGCTGAGTACTTCTGTGCTGTGAGTGATTCTAGGGCTGCAGGCAACAAGCTAACTTT

TGGAGGAGGAACCAGGGTGCTAGTTAAACCAAATATCCAGAACCCTGACCCTGCCGTGTAC

CAGCTGAGAGACTCTAAATCCAGTGACAAGTCTGTCTGCCTATTCACCGATTTTGATTCTCA

AACAAATGTGTCACAAAGTAAGGATTCTGATGTGTATATCACAGACAAAACTGTGCTAGAC

ATGAGGTCTATGGACTTCAAGAGCAACAGTGCTGTGGCCTGGAGCAACAAATCTGACTTTG

CATGTGCAAACGCCTTCAACAACAGCATTATTCCAGAAGACACCTTCTTCCCCAGCCCAGAA

AGTTCCTGTGATGTCAAGCTGGTCGAGAAAAGCTTTGAAACAGATACGAACCTAAACTTTCA

AAACCTGTCAGTGATTGGGTTCCGAATCCTCCTCCTGAAAGTGGCCGGGTTTAATCTGCTCA

TGACGCTGCGGCTGTGGTCCAGCTGA

TCR beta (SEQ ID NO: 10)

ATGGGAATCAGGCTCCTCTGTCGTGTGGCCTTTTGTTTCCTGGCTGTAGGCCTCGTAGATGT

GAAAGTAACCCAGAGCTCGAGATATCTAGTCAAAAGGACGGGAGAGAAAGTTTTTCTGGAA

TGTGTCCAGGATATGGACCATGAAATATGTTCTGGTATCGACAAGACCCAGGTCTGGGGCT

ACGGCTGATCTATTTCTCATATGATGTTAAAATGAAAGAAAAAGGAGATATTCCTGAGGGG

TACAGTGTCTCTAGAGAGAAGAAGGAGCGCTTCTCCCTGATTCTGGAGTCCGCCAGCACCA

ACCAGACATCTATGTACCTCTGTGCCAGCAGATTCCCCGGGACAGCCTATAATTCACCCCTC

CACTTTGGGAATGGGACCAGGCTCACTGTGACAGAGGACCTGAACAAGGTGTTCCCACCCG

AGGTCGCTGTGTTTGAGCCATCAGAAGCAGAGATCTCCCACACCCAAAAGGCCACACTGGT

GTGCCTGGCCACAGGCTTCTTCCCTGACCACGTGGAGCTGAGCTGGTGGGTGAATGGGAAG

GAGGTGCACAGTGGGGTCAGCACGGACCCGCAGCCCCTCAAGGAGCAGCCCGCCCTCAATG

ACTCCAGATACTGCCTGAGCAGCCGCCTGAGGGTCTCGGCCACCTTCTGGCAGAACCCCCGC

AACCACTTCCGCTGTCAAGTCCAGTTCTACGGGCTCTCGGAGAATGACGAGTGGACCCAGG

ATAGGGCCAAACCCGTCACCCAGATCGTCAGCGCCGAGGCCTGGGGTAGAGCAGACTGTGG

CTTTACCTCGGTGTCCTACCAGCAAGGGGTCCTGTCTGCCACCATCCTCTATGAGATCCTGCT

AGGGAAGGCCACCCTGTATGCTGTGCTGGTCAGCGCCCTTGTGTTGATGGCCATGGTCAAGA

GAAAGGATTTCTGA

(b) amino acid sequence of TCR α and β chains (TCR variable regions are in italic, CDR3 regions are in bold)
TCR α chain (SEQ ID NO: 11)

*MLLLLVPVLEVIFTLGGTRAQSVTQLGSHVSVSEGALVLLRCNYSSSVPP*  50

*YLFWYVQYPNQGLQLLLKHITGATLVKGINGFEAEFKKSETSFHLTKPSA*  100

*HMSDAAEYFCAVSDSRAAGNKLTFGGGTRVLVKPNI*QNPDPAVYQLRDSK  150

SSDKSVCLFTDFDSQTNVSQSKDSDVYITDKTVLDMRSMDFKSNSAVAWS  200

```
                                        -continued
NKSDFACANAFNNSIIPEDTFFPSPESSCDVKLVEKSFETDTNLNFQNLS          250

VIGFRILLLKVAGFNLLMTLRLWSS

TCR β chain
                                                   (SEQ ID NO: 12)
MGIRLLCRVAFCFLAVGLVDVKVTQSSRYLVKRTGEKVFLECVQDMDHEN           50

MFWYRQDPGLGLRLIYFSYDVKMKEKGDIPEGYSVSREKKERFSLILESA          100

STNQTSMYLCASRFPGTAYNSPLHFGNGTRLTVTEDLNKVFPPEVAVFEP       150

SEAEISHTQKATLVCLATGFFPDHVELSWWVNGKEVHSGVSTDPQPLKEQ          200

PALNDSRYCLSSRLRVSATFWQNPRNHFRCQVQFYGLSENDEWTQDRAKP          250

VTQIVSAEAWGRADCGFTSVSYQQGVLSATILYEILLGKATLYAVLVSAL          300

VLMAMVKRKDF
```

Description of TCR expression vector. Viral transduction was performed using a murine stem cell virus vector pMSCV-derived plasmid such as pMIG-II and pMIG-w (FIG. 6A). TCR-expressing constructs were inserted into multiple cloning site (MCS) of pMIG plasmid. pMIG plasmids have IRES-GFP after multiple cloning sites so that transduction efficacy is monitored by GFP expression.

To induce equimolar expression of TCR α and β chain proteins, cDNAs encoding TCR α and β chain were connected by a linker sequence including P2A translation skipping site (FIG. 6B(I)). Using this sequence, mRNA is transcribed as one sequence. Because of the ribosomal skipping by P2A sequence, two proteins were translated from the mRNA, to produce TCRβ-P2A fusion protein and P(Pro)-TCRα chain protein.

To avoid potential functional inhibition by P2A peptides added after the TCR β chain protein in TCR-expressing cassette (I), another TCR-expressing cassette that introduces the furin protease recognition site (RAKR) after TCR β chain gene was constructed (FIG. 6B(II). In this expression cassette, additional peptide after the TCR β chain protein is removed by furin protease-mediated cleavage, resulting in expression of TCR α and β chain proteins with minimal modification. In particular, in expression cassettes with or without RAKR sequences, no amino acid is removed relative to the sequences presented herein. However, for a cassette without RAKR (FIG. 6B(I)), GSG linker and P2A sequences are attached to the C-terminus of beta chain, and a Proline (from P2A) is attached to the N-terminus of alpha chain. For a cassette with RAKR (FIG. 6B(II)), Arginine (from RAKR) is attached to the C-terminus of the beta chain and Proline (from P2A) is attached to the N-teminus of alpha chain. Thus, in embodiments, the expression vector encodes a fusion protein comprising TCR amino acid sequences. In embodiments, the only TCR amino acid sequence is selected from the TCR amino acid sequences presented herein.

The TCR-expressing sequences were cloned into multiple cloning site of pMIG plasmid. Retrovirus was produced transiently or stably using GP2-293 and PT67 packaging cell lines purchased from Clontech. Briefly, GP2-293 stably expresses viral gag-pol gene and they transiently produce after co-transfection with pMIG and pVSV-G VSV-G viral envelope-expressing plasmids. PT67 stably expresses viral gag-pol and 10A1 viral envelope genes. After infection with retrovirus produced from GP2-293, PT67 is integrated with the expression construct from pMIG, and therefore stably (continuously) produces retrovirus. In an embodiment, promoter activity of 5'-LTR (long terminal repeat) is used to drive transgene expression. However, other promoters such as EF-1α promoter can be introduced for enhancement of transgene expression.

Infection of retrovirus to PBMC-derived T cells. Whole PBMC were obtained by a density gradient separation method and stored in a liquid nitrogen tank in 90% fetal bovine serum (FBS) and 10% dimethyl sulfoxide (DMSO) until use. PBMC (3–4×10⁶ cells/well in a 24-well culture plate) were polyclonally activated by 10 lag/ml phytohemaglutinin (PHA) for 2 days in culture medium (RPMI1640 medium containing 10% FBS, L-Glutamine, Streptomycin, Penicillin and human recombinant IL-2). 1×10⁵ preactivated PBMC in 100 μl culture medium were added to wells of a 96-well culture plate pre-coated with 20-25 μg/ml retronectin in PBS and blocked with 2% bovine serum albumin (BSA) in PBS. In some experiments, 5 μg/ml anti-CD3 monoclonal antibody (Clone:OKT3) was co-coated with retronectin. 100 μl supernatant containing retrovirus was added to PBMC and incubated for 24 hours. Retrovirus infection was performed 2-3 times every 24 hours. After infection, cells were expanded for 10-14 days and used for functional assays.

Results

High-titer retrovirus-producing PT67 clones were established. The following retrovirus-producing clones were established.

(1) pMIG-II/JM-TCR(II)
(2) pMIG-II/SB95 -TCR(II)
(3) pMIG-w/JM-TCR(I)
(4) pMIG-w/SB95-TCR(I)
(5) pMIG-w/JM-TCR(II)
(6) pMIG-w/SB95-TCR(II)

In the enumerated list above, (I) and (II) refer to expression cassettes without and with the furin protease recognition site (RAKR), respectively, as shown in FIG. 6B. The transduction efficacy measured by GFP expression after a single infection to Jurkat cells was: 60% for (1); 55% for (2); 75% for (3); 75% for (4); 64% for (5); and 62% for (6).

Figure 7:
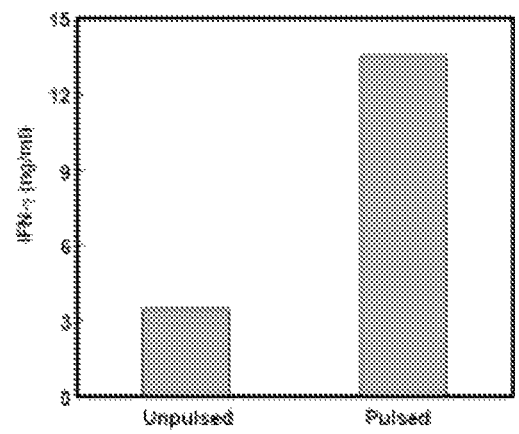
FIG. 7. Polyclonally activated PBMC were transduced with retroviral vector (A: JM-TCR; B: SB95-TCR). They were cocultured with peptide-pulsed (Pulsed) or unpulsed (Unpulsed) HLA-DRB1*01+DPB1*04+ cells for 20 hours. IFN-γ level in the supernatant was measured by ELISA. NY-ESO-1$_{157\text{-}170}$ and NY-ESO-1$_{91\text{-}110}$ peptides were used as the cognate peptides for JM-TCR and SB95-TCR, respectively.
Figure 7:
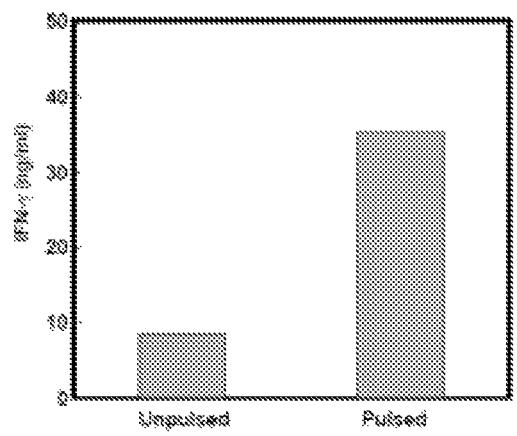

Retrovirus vectors (1) and (2) were transduced to polyclonally activated PBMC. Transduction efficacy as measured by GFP expression was about 40-50%. The reactivity of retrovirally expressed TCR was tested against the same NY-ESO-1-derived cognate peptides (NY-ESO-1:91-110 for SB95-TCR and NY-ESO-1:157-170 for JM-TCR) that were recognized by the original TR-CD4 clones. Significantly more IFN-γ was produced against peptide-pulsed target cells than peptide-unpulsed target cells (FIG. 7), which demonstrates that the cloned TCR genes are functional to transfer the same antigen specificity of original TR-CD4 clones when they are transduced by viral vectors. Functional testing of the remaining TCR expression vectors can be performed in the same manner, such as by infecting activated human peripheral blood mononuclear cells with retrovirus carrying any TCR gene disclosed herein. TCR gene-transduced and untransduced cells can be cocultured for 24 hours with NY-ESO-1-expressing cell lines or tumor samples, and IFN-γ produced by the transduced cells determined using any suitable means, such as by ELISA. IFN-γ level in the supernatant by TCR gene-transduced cells will be higher when co-cultured with cells that express NY-ESO-1 or NY-ESO-1 peptide-pulsed cells, whereas cells cocultured with cells that do not express NY-ESO-1 will have significantly less IFN-γ production. Likewise, negative controls, such as untransduced cells, will have significantly less IFN-γ production. Thus, transfection with a representative recombinant TCR will result in the capability of the cells into which a polynucleotide encoding the TCR to have the same antigen-specificity which directly recognizes NY-ESO-1 antigen on cancer cells.

Although the invention has been described in detail for the purposes of illustration, it is understood that such detail is solely for that purpose, and variations can be made therein by those skilled in the art without departing from the spirit and scope of the invention which is defined by the following claims.

We claim:

1. A modified human T cell comprising a recombinant polynucleotide encoding a T cell receptor (TCR), wherein the recombinant polynucleotide encodes a TCR alpha chain having the sequence of SEQ ID NO:3 and a TCR beta chain having the sequence of SEQ ID NO:4, wherein the T cell is capable of direct recognition of a cancer cell expressing a NY-ESO-1 antigen, wherein the direct recognition of the cancer cell comprises human leukocyte antigen (HLA) class II-restricted binding of the TCR to the NY-ESO-1 antigen expressed by the cancer cell.

2. The modified cell of claim 1, wherein the sequence encoding the alpha chain and/or the beta chain does not comprise introns.

3. An expression vector encoding a T cell receptor (TCR), wherein the TCR comprises an alpha chain having the sequence of SEQ ID NO:3 and a beta chain having the sequence of SEQ ID NO:4.

* * * * *

SEQUENCE LISTING

<160> NUMBER OF SEQ ID NOS: 12

<210> SEQ ID NO 1
<211> LENGTH: 798
<212> TYPE: DNA
<213> ORGANISM: human

<400> SEQUENCE: 1

```
atgaagttgg tgacaagcat tactgtactc ctatctttgg gtattatggg tgatgctaag      60
accacacagc caaattcaat ggagagtaac gaagaagagc tgttcactt gccttgtaac     120 cactccacaa tcagtggaac tgattacata cattggtatc gacagcttcc ctcccagggt     180
ccagagtacg tgattcatgg tcttacaagc aatgtgaaca acagaatggc ctctctggca     240
atcgctgaag acagaaagtc cagtaccttg atcctgcacc gtgctacctt gagagatgct     300
gctgtgtact actgcatccc taataacaat gacatgcgct ttggagcagg gaccagactg     360
acagtaaaac caaatatcca gaaccctgac cctgccgtgt accagctgag agactctaaa     420
tccagtgaca agtctgtctg cctattcacc gattttgatt ctcaaacaaa tgtgtcacaa     480
agtaaggatt ctgatgtgta tatcacagac aaaactgtgc tagacatgag gtctatggac     540
ttcaagagca acagtgctgt ggcctggagc aacaaatctg actttgcatg tgcaaacgcc     600
ttcaacaaca gcattattcc agaagacacc ttcttcccca gcccagaaag ttcctgtgat     660
gtcaagctgg tcgagaaaag ctttgaaaca gatacgaacc taaactttca aaacctgtca     720
gtgattgggt tccgaatcct cctcctgaaa gtggccgggt taatctgct catgacgctg     780 cggctgtggt ccagctga                                                   798
```

<210> SEQ ID NO 2
<211> LENGTH: 798
<212> TYPE: DNA
<213> ORGANISM: human

<400> SEQUENCE: 2

```
atgaagttgg tgacaagcat tactgtactc ctatctttgg gtattatggg tgatgctaag      60
accacacagc caaattcaat ggagagtaac gaagaagagc tgttcactt gccttgtaac     120 cactccacaa tcagtggaac tgattacata cattggtatc gacagcttcc ctcccagggt     180
ccagagtacg tgattcatgg tcttacaagc aatgtgaaca acagaatggc ctctctggca     240
atcgctgaag acagaaagtc cagtaccttg atcctgcacc gtgctacctt gagagatgct     300
gctgtgtact actgcatccc taataacaat gacatgcgct ttggagcagg gaccagactg     360
acagtaaaac caaatatcca gaaccctgac cctgccgtgt accagctgag agactctaaa     420
tccagtgaca agtctgtctg cctattcacc gattttgatt ctcaaacaaa tgtgtcacaa     480
```

```
agtaaggatt ctgatgtgta tatcacagac aaaactgtgc tagacatgag gtctatggac    540
ttcaagagca acagtgctgt ggcctggagc aacaaatctg actttgcatg tgcaaacgcc    600
ttcaacaaca gcattattcc agaagacacc ttcttcccca gcccagaaag ttcctgtgat    660
gtcaagctgg tcgagaaaag ctttgaaaca gatacgaacc taaactttca aaacctgtca    720
gtgattgggt tccgaatcct cctcctgaaa gtggccgggt ttaatctgct catgacgctg    780
cggctgtggt ccagctga                                                  798
```

```
<210> SEQ ID NO 3
<211> LENGTH: 265
<212> TYPE: PRT
<213> ORGANISM: human

<400> SEQUENCE: 3

Met Lys Leu Val Thr Ser Ile Thr Val Leu Leu Ser Leu Gly Ile Met
  1               5                  10                  15

Gly Asp Ala Lys Thr Thr Gln Pro Asn Ser Met Glu Ser Asn Glu Glu
             20                  25                  30

Glu Pro Val His Leu Pro Cys Asn His Ser Thr Ile Ser Gly Thr Asp
         35                  40                  45

Tyr Ile His Trp Tyr Arg Gln Leu Pro Ser Gln Gly Pro Glu Tyr Val
     50                  55                  60

Ile His Gly Leu Thr Ser Asn Val Asn Asn Arg Met Ala Ser Leu Ala
 65                  70                  75                  80

Ile Ala Glu Asp Arg Lys Ser Ser Thr Leu Ile Leu His Arg Ala Thr
                 85                  90                  95

Leu Arg Asp Ala Ala Val Tyr Tyr Cys Ile Pro Asn Asn Asn Asp Met
            100                 105                 110

Arg Phe Gly Ala Gly Thr Arg Leu Thr Val Lys Pro Asn Ile Gln Asn
        115                 120                 125

Pro Asp Pro Ala Val Tyr Gln Leu Arg Asp Ser Lys Ser Ser Asp Lys
    130                 135                 140

Ser Val Cys Leu Phe Thr Asp Phe Asp Ser Gln Thr Asn Val Ser Gln
145                 150                 155                 160

Ser Lys Asp Ser Asp Val Tyr Ile Thr Asp Lys Thr Val Leu Asp Met
                165                 170                 175

Arg Ser Met Asp Phe Lys Ser Asn Ser Ala Val Ala Trp Ser Asn Lys
            180                 185                 190

Ser Asp Phe Ala Cys Ala Asn Ala Phe Asn Asn Ser Ile Ile Pro Glu
        195                 200                 205

Asp Thr Phe Phe Pro Ser Pro Glu Ser Ser Cys Asp Val Lys Leu Val
    210                 215                 220

Glu Lys Ser Phe Glu Thr Asp Thr Asn Leu Asn Phe Gln Asn Leu Ser
225                 230                 235                 240

Val Ile Gly Phe Arg Ile Leu Leu Leu Lys Val Ala Gly Phe Asn Leu
                245                 250                 255

Leu Met Thr Leu Arg Leu Trp Ser Ser
            260                 265

<210> SEQ ID NO 4
<211> LENGTH: 310
<212> TYPE: PRT
<213> ORGANISM: human

<400> SEQUENCE: 4
```

```
Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Phe Pro Arg Glu Pro Asn Tyr Gly Tyr Thr Phe Gly Ser Gly Thr
            115                 120                 125

Arg Leu Thr Val Val Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
        290                 295                 300

Val Lys Arg Lys Asp Phe
305                 310

<210> SEQ ID NO 5
<211> LENGTH: 780
<212> TYPE: DNA
<213> ORGANISM: human

<400> SEQUENCE: 5
atggcccaga cagtcactca gtctcaacca gagatgtctg tgcaggaggc agagactgtg      60
accctgagtt gcacatatga caccagtgag aataattatt atttgttctg gtacaagcag     120
cctcccagca ggcagatgat tctcgttatt cgccaagaag cttataagca acagaatgca     180
acggagaatc gtttctctgt gaacttccag aaagcagcca atccttcag tctcaagatc     240 tcagactcac agctggggga cactgcgatg tatttctgtg cttttctcgag agggagtgga     300 ggtagcaact ataaactgac atttggaaaa ggaactctct taaccgtgaa tccaaatatc     360
```

```
cagaaccctg accctgccgt gtaccagctg agagactcta aatccagtga caagtctgtc    420
tgcctattca ccgattttga ttctcaaaca aatgtgtcac aaagtaagga ttctgatgtg    480
tatatcacag acaaaactgt gctagacatg aggtctatgg acttcaagag caacagtgct    540
gtggcctgga gcaacaaatc tgactttgca tgtgcaaacg ccttcaacaa cagcattatt    600
ccagaagaca ccttcttccc cagcccagaa agttcctgtg atgtcaagct ggtcgagaaa    660
agctttgaaa cagatacgaa cctaaacttt caaaacctgt cagtgattgg gttccgaatc    720
ctcctcctga aagtggccgg gtttaatctg ctcatgacgc tgcggctgtg gtccagctga    780
```

<210> SEQ ID NO 6
<211> LENGTH: 942
<212> TYPE: DNA
<213> ORGANISM: human

<400> SEQUENCE: 6

```
atgggcacca ggctcctctt ctgggtggcc ttctgtctcc tgggggcaga tcacacagga     60
gctggagtct cccagtcccc cagtaacaag gtcacagaga agggaaagga tgtagagctc    120
aggtgtgatc caatttcagg tcatactgcc ctttactggt accgacagag cctggggcag    180
ggcctggagt ttttaattta cttccaaggc aacagtgcac agacaaatc agggctgccc    240
agtgatcgct ctctgcagag aggactgggg gatccgtctc ccactctgac gatccagcgc    300
acacagcagg aggactcggc cgtgtatctc tgtgccagca gcttagtccc cgacagtgcc    360
tacgagcagt acttcgggcc gggcaccagg ctcacggtca cagaggacct gaaaaacgtg    420
ttcccacccg aggtcgctgt gtttgagcca tcagaagcag agatctccca caccaaaag    480
gccacactgg tatgcctggc cacaggcttc taccccgacc acgtggagct gagctggtgg    540
gtgaatggga aggaggtgca cagtggggtc agcacgggac cgcagcccct caaggagcag    600
cccgccctca tgactccaga atactgcctg agcagccgcc tgagggtctc ggccaccttc    660
tggcagaacc ccgcgaacca cttccgctgt caagtccagt tctacgggct ctcggagaat    720
gacgagtgga cccaggatag gccaaaacct gtcacccaga tcgtcagcgc cgaggcctgg    780
ggtagagcag actgtggctt cacctccgag tcttaccagc aagggggtcct gtctgccacc    840
atcctctatg agatcttgct agggaaggcc accttgtatg ccgtgctggt cagtgccctc    900
gtgctgatgg ccatggtcaa gagaaaggat tccagaggct ag                       942
```

<210> SEQ ID NO 7
<211> LENGTH: 259
<212> TYPE: PRT
<213> ORGANISM: human

<400> SEQUENCE: 7

```
Met Ala Gln Thr Val Thr Gln Ser Gln Pro Glu Met Ser Val Gln Glu
1               5                   10                  15

Ala Glu Thr Val Thr Leu Ser Cys Thr Tyr Asp Thr Ser Glu Asn Asn
            20                  25                  30

Tyr Tyr Leu Phe Trp Tyr Lys Gln Pro Pro Ser Arg Gln Met Ile Leu
        35                  40                  45

Val Ile Arg Gln Glu Ala Tyr Lys Gln Gln Asn Ala Thr Glu Asn Arg
    50                  55                  60

Phe Ser Val Asn Phe Gln Lys Ala Ala Lys Ser Phe Ser Leu Lys Ile
65                  70                  75                  80

Ser Asp Ser Gln Leu Gly Asp Thr Ala Met Tyr Phe Cys Ala Phe Ser
```

```
                85                  90                  95
Arg Gly Ser Gly Gly Ser Asn Tyr Lys Leu Thr Phe Gly Lys Gly Thr
            100                 105                 110

Leu Leu Thr Val Asn Pro Asn Ile Gln Asn Pro Asp Pro Ala Val Tyr
            115                 120                 125

Gln Leu Arg Asp Ser Lys Ser Ser Asp Lys Ser Val Cys Leu Phe Thr
130             135                 140

Asp Phe Asp Ser Gln Thr Asn Val Ser Gln Ser Lys Asp Ser Asp Val
145                 150                 155                 160

Tyr Ile Thr Asp Lys Thr Val Leu Asp Met Arg Ser Met Asp Phe Lys
                165                 170                 175

Ser Asn Ser Ala Val Ala Trp Ser Asn Lys Ser Asp Phe Ala Cys Ala
            180                 185                 190

Asn Ala Phe Asn Asn Ser Ile Ile Pro Glu Asp Thr Phe Phe Pro Ser
            195                 200                 205

Pro Glu Ser Ser Cys Asp Val Lys Leu Val Glu Lys Ser Phe Glu Thr
            210                 215                 220

Asp Thr Asn Leu Asn Phe Gln Asn Leu Ser Val Ile Gly Phe Arg Ile
225                 230                 235                 240

Leu Leu Leu Lys Val Ala Gly Phe Asn Leu Leu Met Thr Leu Arg Leu
                245                 250                 255

Trp Ser Ser

<210> SEQ ID NO 8
<211> LENGTH: 313
<212> TYPE: PRT
<213> ORGANISM: human

<400> SEQUENCE: 8

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
                20                  25                  30

Glu Lys Gly Lys Asp Val Glu Leu Arg Cys Asp Pro Ile Ser Gly His
            35                  40                  45

Thr Ala Leu Tyr Trp Tyr Arg Gln Ser Leu Gly Gln Gly Leu Glu Phe
        50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Val Pro Asp Ser Ala Tyr Glu Gln Tyr Phe Gly Pro Gly
            115                 120                 125

Thr Arg Leu Thr Val Thr Glu Asp Leu Lys Asn Val Phe Pro Pro Glu
130             135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
```

```
            195                 200                 205
Cys Leu Ser Ser Arg Leu Arg Val Ser Ala Thr Phe Trp Gln Asn Pro
        210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Glu Ser Tyr
        260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
        290                 295                 300

Met Val Lys Arg Lys Asp Ser Arg Gly
305                 310

<210> SEQ ID NO 9
<211> LENGTH: 828
<212> TYPE: DNA
<213> ORGANISM: human

<400> SEQUENCE: 9
atgctcctgc tgctcgtccc agtgctcgag gtgatttta  ccctgggagg aaccagagcc      60
cagtcggtga cccagcttgg cagccacgtc tctgtctctg agggagccct ggttctgctg     120
aggtgcaact actcatcgtc tgttccacca tatctcttct ggtatgtgca ataccccaac     180
caaggactcc agcttctcct gaagcacaca acaggggcca cctggttaa  aggcatcaac     240 ggttttgagg ctgaatttaa gaagagtgaa acctccttcc acctgacgaa accctcagcc     300
catatgagcg acgcggctga gtacttctgt gctgtgagtg attctagggc tgcaggcaac     360
aagctaactt ttggaggagg aaccagggtg ctagttaaac caaatatcca gaaccctgac     420
cctgccgtgt accagctgag agactctaaa tccagtgaca agtctgtctg cctattcacc     480
gattttgatt ctcaaacaaa tgtgtcacaa agtaaggatt ctgatgtgta tatcacagac     540
aaaactgtgc tagacatgag gtctatggac ttcaagagca cagtgctgt  ggcctggagc     600 aacaaatctg actttgcatg tgcaaacgcc ttcaacaaca gcattattcc agaagacacc     660
ttcttcccca gcccagaaag ttcctgtgat gtcaagctgg tcgagaaaag ctttgaaaca     720
gatacgaacc taaactttca aaacctgtca gtgattgggt ccgaatcctc cctcctgaaa     780
gtggccgggt taatctgct  catgacgctg cggctgtggt ccagctga               828

<210> SEQ ID NO 10
<211> LENGTH: 936
<212> TYPE: DNA
<213> ORGANISM: human

<400> SEQUENCE: 10
atgggaatca ggctcctctg tcgtgtggcc ttttgtttcc tggctgtagg cctcgtagat      60
gtgaaagtaa cccagagctc gagatatcta gtcaaaagga cgggagagaa agttttctg     120 gaatgtgtcc aggatatgga ccatgaaaat atgttctggt atcgacaaga cccaggtctg     180 ggctacggc  tgatctattt ctcatatgat gttaaaatga agaaaaagg  agatattcct     240 gaggggtaca gtgtctctag agagaagaag gagcgcttct ccctgattct ggagtccgcc     300
agcaccaacc agacatctat gtacctctgt gccagcagat tccccgggac agcctataat     360
```

```
tcacccctcc actttgggaa tgggaccagg ctcactgtga cagaggacct gaacaaggtg    420
ttcccacccg aggtcgctgt gtttgagcca tcagaagcag agatctccca cacccaaaag    480
gccacactgg tgtgcctggc cacaggcttc ttccctgacc acgtggagct gagctggtgg    540
gtgaatggga aggaggtgca cagtggggtc agcacggacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt tacctcggtg tcctaccagc aagggtcct gtctgccacc    840 atcctctatg agatcctgct agggaaggcc accctgtatg ctgtgctggt cagcgccctt    900
gtgttgatgg ccatggtcaa gagaaaggat ttctga                              936
```

<210> SEQ ID NO 11
<211> LENGTH: 275
<212> TYPE: PRT
<213> ORGANISM: human

<400> SEQUENCE: 11

```
Met Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser
                20                  25                  30

Ser Glu Gly Ala Leu Val Leu Leu Arg Cys Asn Tyr Ser Ser Val
            35                  40                  45

Pro Pro Tyr Leu Phe Trp Tyr Val Gln Tyr Pro Asn Gln Gly Leu Gln
50                  55                  60

Leu Leu Leu Lys His Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
                100                 105                 110

Ser Asp Ser Arg Ala Ala Gly Asn Lys Leu Thr Phe Gly Gly Gly Thr
            115                 120                 125

Arg Val Leu Val Lys Pro Asn Ile Gln Asn Pro Asp Pro Ala Val Tyr
130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270
```

Trp Ser Ser
        275

<210> SEQ ID NO 12
<211> LENGTH: 311
<212> TYPE: PRT
<213> ORGANISM: human

<400> SEQUENCE: 12

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Phe Pro Gly Thr Ala Tyr Asn Ser Pro Leu His Phe Gly Asn Gly
        115                 120                 125

Thr Arg Leu Thr Val Thr Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310